(12) United States Patent
Senetar et al.

(10) Patent No.: US 7,423,191 B2
(45) Date of Patent: Sep. 9, 2008

(54) METHOD AND SYSTEM FOR CATALYTICALLY CONVERTING OXYGENATES AND REGENERATING AND STRIPPING CATALYST

(75) Inventors: John J. Senetar, Naperville, IL (US); Richard A. Johnson, II, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 495 days.

(21) Appl. No.: 11/014,131

(22) Filed: Dec. 16, 2004

(65) Prior Publication Data

US 2006/0135835 A1    Jun. 22, 2006

(51) Int. Cl.
*C07C 1/00* (2006.01)
*B01J 20/34* (2006.01)

(52) U.S. Cl. .......... 585/640; 585/639; 502/20; 502/34; 502/38; 502/514

(58) Field of Classification Search ......... 585/638–640; 502/20, 34, 38, 54, 514
See application file for complete search history.

(56) References Cited

U.S. PATENT DOCUMENTS

| | | | |
|---|---|---|---|
| 3,928,483 A | 12/1975 | Chang et al. | 260/668 R |
| 4,025,575 A | 5/1977 | Chang et al. | 260/682 |
| 4,051,013 A | 9/1977 | Strother | 208/78 |
| 4,052,479 A | 10/1977 | Chang et al. | 260/682 |
| 4,252,479 A | 2/1981 | Scherfenberg | 406/182 |
| 4,447,669 A | 5/1984 | Hamon et al. | 585/640 |
| 4,496,786 A | 1/1985 | Santilli et al. | 585/640 |
| 4,499,314 A | 2/1985 | Seddon et al. | 585/408 |
| 4,547,616 A | 10/1985 | Avidan et al. | 585/640 |
| 4,677,242 A | 6/1987 | Kaiser | 585/638 |
| 4,843,183 A | 6/1989 | Inui | 585/640 |
| 4,861,938 A | 8/1989 | Lewis et al. | 585/640 |
| 4,973,792 A | 11/1990 | Lewis et al. | 585/638 |
| 5,095,163 A | 3/1992 | Barger | 585/640 |
| 5,126,308 A | 6/1992 | Barger et al. | 502/214 |
| 5,191,141 A | 3/1993 | Barger et al. | 585/640 |
| 6,121,503 A * | 9/2000 | Janssen et al. | 585/640 |
| 6,441,262 B1 * | 8/2002 | Fung et al. | 585/640 |
| 6,965,057 B2 | 11/2005 | Beech, Jr. et al. | 585/640 |

* cited by examiner

*Primary Examiner*—Glenn Caldarola
*Assistant Examiner*—In Suk Bullock
(74) *Attorney, Agent, or Firm*—James C Paschall

(57) ABSTRACT

A method of converting oxygenate-containing feedstock to light olefins comprises charging a reactor with catalyst, feeding the feedstock into the reactor, contacting the feedstock with the catalyst and converting the feedstock to olefins while depositing byproducts on catalyst resulting in spent catalyst, regenerating the spent catalyst by combustion gases, and stripping the regenerated catalyst of gases entrained in the regenerating step. The stripping step is accomplished using nitrogen gas to strip the entrained gases from the regenerate catalyst. In one embodiment, regenerated catalyst is passed through a regenerated catalyst stripper before it is returned to the reactor.

7 Claims, 1 Drawing Sheet

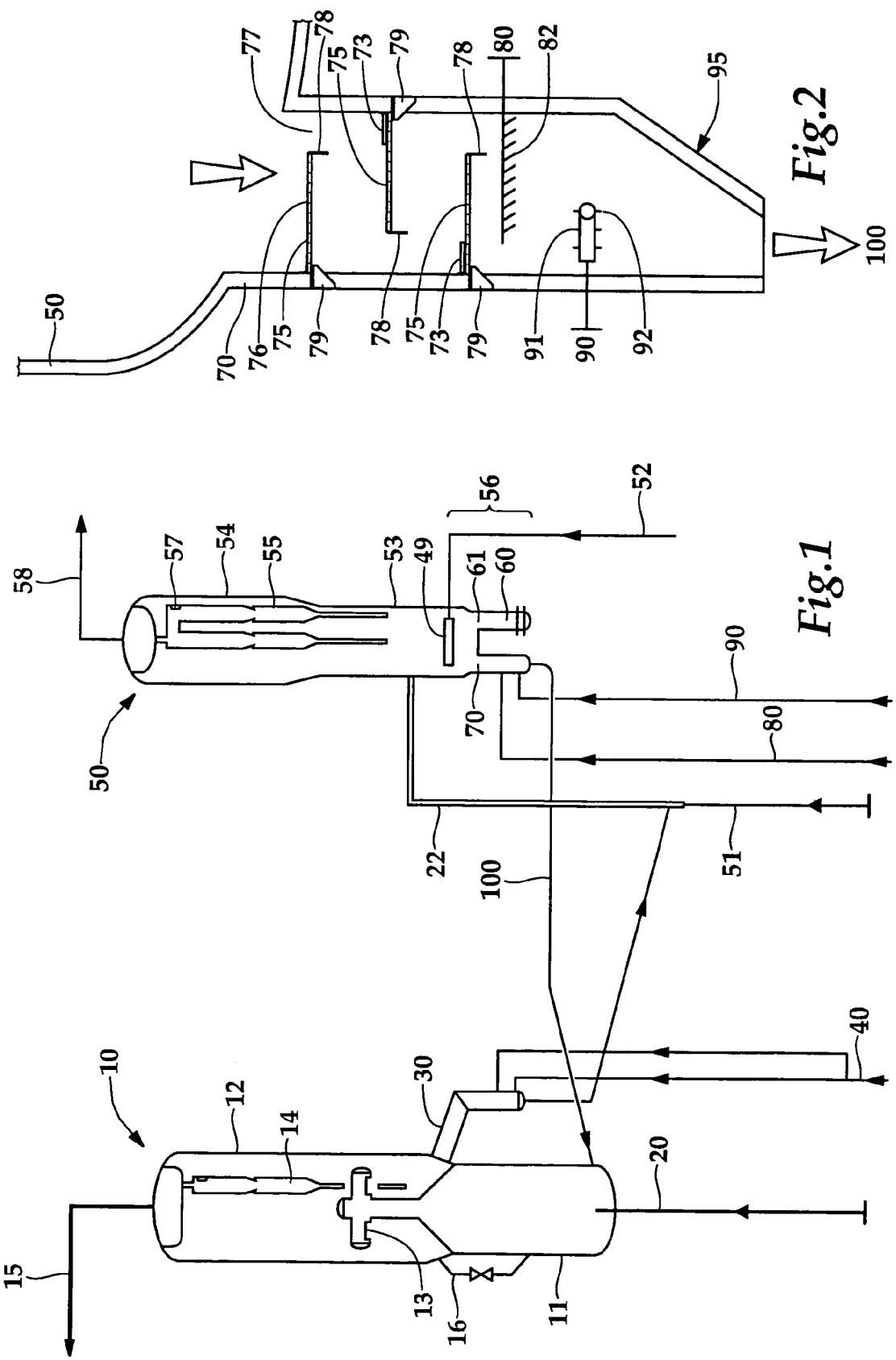

METHOD AND SYSTEM FOR CATALYTICALLY CONVERTING OXYGENATES AND REGENERATING AND STRIPPING CATALYST

BACKGROUND OF THE INVENTION

This invention relates to a method and system for treating regenerated catalyst in an oxygenate to olefin conversion process.

DESCRIPTION OF THE PRIOR ART

Light olefins have traditionally been produced through the process of steam or catalytic cracking. Because of the limited availability and high cost of petroleum sources, the cost of producing light olefins from such petroleum sources has been steadily increasing. Light olefins serve as feeds for the production of numerous chemicals.

The search for alternative materials for light olefin production has led to the use of oxygenates such as alcohols and, more particularly, to the use of methanol, ethanol, and higher alcohols or their derivatives. Molecular sieves such as microporous crystalline zeolite and non-zeolitic catalysts, particularly silicoaluminophosphates (SAPO), are known to promote the conversion of oxygenates to hydrocarbon mixtures in a reactor. Numerous patents describe this process for various types of these catalysts: U.S. Pat. Nos. 3,928,483; 4,025,575; 4,052,479; 4,496,786; 4,547,616; 4,677,242; 4,843,183; 4,499,314; 4,447,669; 5,095,163; 5,191,141; 5,126,308; 4,973,792; and 4,861,938.

When a catalyst is exposed to oxygenates, such as methanol, to promote the reaction to olefins, carbonaceous material (coke) is generated and deposited on the catalyst. Accumulation of coke deposits interferes with the catalyst's ability to promote the reaction. As the amount of coke deposit increases, the catalyst loses activity and less of the feedstock is converted to the desired olefin product. The step of regeneration removes the coke from the catalyst by combustion with oxygen, restoring the catalytic activity of the catalyst. The regenerated catalyst may then be exposed again to oxygenates to promote the conversion to olefins.

The exposed catalyst with coke deposit is continuously withdrawn from the reactor and regenerated in a regenerator and then returned to the reactor. The catalyst is then directed to the regenerator where combustion with oxygen-containing air burs off the coke deposit on the catalyst. The combustion air used in regenerating the catalyst leaves carbon monoxide, oxygen, and carbon dioxide gases entrained in the catalyst. Oxygen is not a natural byproduct of the oxygenate-to-olefin reaction and when introduced through entrainment with regenerated catalyst creates processing difficulties downstream. The presence of oxygen will increase the amount of contaminant carbon dioxide and carbon monoxide formed among the desired product. Carbon dioxide and carbon monoxide entrained from the regenerator also significantly increase the concentration of these contaminants in the olefin product.

Carbon dioxide is a contaminant in polymer grade ethylene and propylene and is removed using caustic scrubbing. By eliminating the entrained carbon dioxide from the regenerated catalyst, the caustic consumption in the downstream caustic scrubber is significantly reduced. Eliminating the entrained oxygen has the benefit of reducing the potential for fouling in the downstream caustic scrubber and reducing operational problems in the downstream acetylene converter. Increased carbon monoxide increases the operating temperature of the acetylene converter and therefore narrows the operating range between normal operation and the maximum allowable temperature to avoid thermal runway.

SUMMARY OF THE INVENTION

A method is disclosed for stripping entrained gases from regenerated catalyst used in converting an oxygenate-containing feedstock to olefins comprising regenerating a catalyst and then stripping the regenerated catalyst. In another aspect, a method is also disclosed for converting oxygenate-containing feedstock to olefins comprising charging a reactor with catalyst, feeding the oxygenate-containing feedstock into the reactor, contacting the oxygenate-containing feedstock with the catalyst in the reactor and converting the oxygenate-containing feedstock to olefins while spending the catalyst, regenerating the spent catalyst, and stripping the regenerated catalyst of gases entrained during the regeneration step. In another aspect of the method, nitrogen gas strips the regenerated catalyst. In a further aspect, hydrocarbons are stripped from the catalyst before the regenerating step.

A system also is disclosed for regenerating catalyst used in converting oxygenate-containing feedstock to olefins comprising a regenerator and a regenerated catalyst stripper having a regenerated catalyst inlet, a stripping gas distributor and a stripped regenerated catalyst outlet. In one embodiment, the stripper has a plurality of baffles to enhance contact between the stripping gas and the catalyst. The catalyst inlet is preferably near the top of the stripper.

BRIEF DESCRIPTION OF THE DRAWINGS

FIG. 1 is a schematic diagram of a system and method for using, regenerating, and stripping a catalyst used in an oxygenate-containing feedstock to olefins conversion process.

FIG. 2 is a side view of the regenerated catalyst stripper of FIG. 1.

DETAILED DESCRIPTION OF THE INVENTION

Oxygenate-containing feedstock may be converted to light olefins in a catalytic reaction and the catalyst may be regenerated and stripped of entrained gases before being returned to catalyze further reactions. Feedstock comprising oxygenate, such as methanol, may be contacted with a catalyst containing a molecular sieve in reactor 10. Catalytic activity should be maintained at a predetermined level for oxygenate-containing feedstock to be continuously converted to olefins. Deposits on catalyst that impair catalytic activity should be removed without disrupting conditions for the reaction of oxygenate-containing feedstock to olefins. Fluidization of catalyst particles by various gaseous streams allows transport of catalyst between reactor 10, stripper 30, regenerator 50, and stripper 70. One oxygenate-containing feedstock may be methanol. The methanol to olefin (MTO) conversion process may be a vapor phase, fluid catalytic process that converts methanol to olefins, primarily ethylene and propylene. Feedstock may be commercial grade methanol, crude methanol or any combination of the two. Crude methanol may be an unrefined product from a methanol synthesis unit. Feed comprising methanol and water blend may have methanol between about 65% and about 90% by weight. More preferably, feed comprising methanol and water blend may have methanol between about 78% and about 82% by weight. Most preferably, feed comprising methanol and water blend may be about 80% methanol by weight. As seen in FIG. 1, MTO reactor 10 may be a fluid catalytic design. Coke may be a byproduct of the MTO process that accumulates on catalyst during contact with oxygenate-containing feedstock. Catalyst becomes spent as coke deposits accumulate on the catalyst and decrease its ability to convert oxygenate-feedstock to olefins. Therefore, spent catalyst from reactor 10 may be continuously regenerated to maintain the desired activity. The catalyst may be silicoaluminophosphate (SAPO), having a tetrahedral unit framework forming numerous pores to best contact methanol feed during conversion to olefins.

At least a portion of the spent catalyst may be continuously drawn out of reactor 10 for regeneration. Before the spent catalyst may be regenerated, hydrocarbons may be stripped from the spent catalyst in reactor stripper 30 using steam. The spent catalyst may be transferred to regenerator 50 where the coke may be removed from the catalyst, resulting in a regenerated catalyst. Gases from regeneration may be entrained in the regenerated catalyst when the catalyst is removed from regenerator 50 and the entrained gases may be disruptive to reactor 10 conditions for converting methanol to olefins.

The catalyst may preferably have a void fraction between about 0.2 and about 0.5 and more preferably be between about 0.3 and about 0.4. The coke on the spent catalyst may typically be between about 2 wt-% and about 20 wt-% and more typically be between about 3 wt-% and about 10 wt-% The coke on the regenerated catalyst may preferably be between about 0.1 wt-% and about 0.5 wt-% and more preferably be between about 0.2 wt-% and about 0.4 wt-% The percentage of coke oxidized may preferably be at least 80 wt-%, more preferably be at least about 85 wt-%, and most preferably be at least about 90 wt-%.

Much of entrained gases used during regeneration may be removed from the regenerated catalyst after regeneration by cyclone 55 within regenerator 50, but as seen in example below, a significant amount of entrained gases remain with regenerated catalyst when it leaves regenerator 50. These entrained gases include gases which may be adsorbed onto the catalyst, located within its pore structure or simply carried in interstitial volume between catalyst particles. Regenerated catalyst may be transferred to regenerated catalyst stripper 70 before being returned to reactor 10 where entrained gases remaining with the catalyst from the regenerating step are stripped by a stripping gas. In one embodiment, the entrained gases which may comprise carbon dioxide ($CO_2$), carbon monoxide (CO), and oxygen ($O_2$) are removed by nitrogen ($N_2$) gas. Use of a CO oxidation promoter additive in the catalyst will reduce the relative ratio of CO to $CO_2$ in the entrained gases.

Oxides of nitrogen may be formed in regenerator 50 and can be entrained with catalyst delivered into reactor 10. Oxides of nitrogen (NOx) can create a hazard in the downstream cryogenic recovery section. NOx may include nitric oxide (NO), nitrogen dioxide ($NO_2$), nitrogen trioxide ($N_2O_2$), and dinitrogen tetroxide ($N_{2O4}$). Trace amounts of NOx can react with hydrocarbons to form unstable compounds. These compounds are known as NOx gums, nitrogenous gums, vapor phase gums, etc., and accumulate over time in cryogenic equipment used for purifying ethylene. NOx gums can lead to a risk of explosion when equipment is taken offline and warmed to ambient conditions for maintenance.

Stripped regenerated catalyst may be returned to reactor 10 for further conversion of methanol to olefins. An absence or reduction of entrained gases with regenerated catalyst helps conversion of methanol to olefins by reducing byproducts formed within reactor 10 and cutting down costs on downstream product recovery.

Nitrogen directed to the regenerated catalyst stripper to strip the entrained gases from the regeneration step may be between about 0.5 and about 8.0 kg of nitrogen per 1000 kg of catalyst. Preferably, the nitrogen directed to the regenerated catalyst stripper may be between about 2.0 and about 5.0 kg of nitrogen per 1000 kg of catalyst. More preferably, the nitrogen directed to the regenerated catalyst stripper may be between about 3.0 and about 4.0 kg of nitrogen per 1000 kg of catalyst.

A method of processing catalyst exposed in a conversion reaction of oxygenate-containing feedstock to olefins includes regenerating the exposed catalyst and stripping the regenerated catalyst of gases entrained during the regenerating step.

In one embodiment of a method for processing oxygenate-containing feedstock to olefins, the catalyst for converting oxygenate-containing feedstock to olefins travels a route from reactor 10 to a hydrocarbon stripper 30 to regenerator 50 to regenerated catalyst stripper 70 back to reactor 10. A method of regenerating a catalyst used in converting oxygenate-containing feedstock to olefins includes: charging reactor 10 with catalyst, feeding the oxygenate-containing feedstock into reactor 10, contacting the oxygenate-containing feedstock with the catalyst in reactor 10 and converting the feedstock to olefins while spending the catalyst, regenerating the spent catalyst, and stripping the regenerated catalyst of gases entrained during the regenerating step. In another aspect of the method, hydrocarbon vapors are stripped from the spent catalyst before the regeneration step. Entrained gases may include oxygen, carbon dioxide, and carbon monoxide. The method may also comprise the regenerated catalyst stripping gases combining with the combustion gases and discharging from a common outlet.

As seen in FIG. 1, reactor 10 comprises a lower reactor section 11 and an upper reactor section 12. Lower reactor section 11, where the process reaction actually occurs, consists of a feed distributor 20, a fluidized bed of catalyst and an outlet riser 13. Upper reactor section 12 may be primarily the vapor/catalyst separation zone. After the preliminary disengagement at the top of the outlet riser 13, cyclone 14 carries the separation to a greater degree. Separated catalyst may be continually recycled from upper reactor section 12 back down to lower reactor section 11, via recirculation conduit 16 through a slide valve, to maintain the desired catalyst density in lower reactor 11. The olefins and byproducts produced by the reaction are discharged from reactor 10 by conduit 15 which directs the olefins and byproducts to a product recovery process. The temperature range in the reactor is preferred to be between about 440° C. and about 520° C. The more preferred range of the temperature in the reactor is between about 450° C. and about 500° C. The preferred feed temperature range is between about 120° C. and about 200° C. More preferably the feed temperature range is between about 180° C. and 200° C.

Hydrocarbons also may be included as part of the oxygenate-containing feedstock. Hydrocarbons included in the feedstock are adsorbed or trapped in the molecular sieve structure of the catalyst during conversion of oxygenate feed to olefins. Hydrocarbons may include olefins, reactive paraffins, reactive aromatics, or mixtures thereof. The catalyst exposed to the oxygenate-containing feedstock in the reactor becomes spent catalyst, and may be withdrawn from reactor 10 and directed to reactor stripper 30 situated adjacent to reactor 10.

The stripping process removes the volatile organic components which may be entrained with the catalyst prior to entering regenerator 50. A stripping gas may be passed over the catalyst in reactor stripper 30. In one embodiment the stripping gas comprises steam directed into the reactor stripper 30 via lines 40.

The entrained steam traveling from reactor stripper 30 to regenerator 50 may typically be between about 0.40 m$^3$/m$^3$ catalyst and 0.80 m$^3$/m$^3$ catalyst measured at operating conditions. More typically the range for entrained steam is between about 0.60 m$^3$/m$^3$ catalyst and 0.70 m$^3$/m$^3$ catalyst.

MTO regenerator 50 may be a bubbling (turbulent) bed type of design. Regenerator 50 may comprise a vessel containing a distributor 49 fed by combustion gas line 52, a fluidized bed of catalyst and cyclones 55. Main air blower on line 52 or pressurized air supplies combustion gas to regenerator 50. Catalyst regeneration may be exothermic. The heat of combustion of the coke may be combusted from regenerator 50 by vaporizing water circulated through tubes in regenerator catalyst coolers 60.

Combustion air may contain oxygen (O$_2$) or other oxidants. It may be preferred to supply oxygen in the form of air. The air can be diluted with nitrogen, CO$_2$, flue gas, or steam. Coke deposits are removed from the catalyst during regeneration, forming a regenerated catalyst.

In one embodiment, regenerator 50 comprises a fluid bed section 53, an upper disengaging section 54 and a lower section 56 comprising regenerated catalyst stripping section 70 and regenerator catalyst coolers 60. In operation, regenerator 50 contacts spent catalyst transferred from reactor 10 by an exposed catalyst standpipe 22 with compressed air from distributor 51. Contact with oxygen combusts coke from the catalyst as it passes upwardly through fluid bed section 53. A small portion of the catalyst remains entrained with the combustion gases and enters inlet 57 of cyclones 55 which separate much of the entrained catalyst from the combustion gases. Catalyst travels to the lower section 56 via the dip legs on cyclones 55.

In one embodiment, typical flue gas in regenerator 50 may comprise as follows by percentage volume: 2-11% H$_2$O, 3-7% O$_2$, 75-80% N$_2$, and 10-15% CO$_2$. There may be residual CO in the flue gas within regenerator 50. Combustion flue gases are discharged from regenerator 50 via conduit 58.

Catalyst enters regenerator catalyst cooler 60 through an opening 61. Catalyst entering cooler 60 contacts the outer surface of a heat exchange tube as it passes downwardly through the cooler and returns to fluid bed section 53 via a conduit. Cooler 60 may be cooled by vaporizing water into steam. Heat exchange tubes are bayonet style tubes having an outer tube that contacts the catalyst and an inner tube for circulating a cooling fluid. Fluidizing gas comprising air and distributed by a plurality of conduits enter cooler 60. Fluidizing gas passes upwardly through the cooler 60 and through opening 61 into upper disengaging section 54. The fluidizing gas requirement will depend on the amount of coke being combusted from the catalyst.

To prevent the entry of large objects such as agglomerated masses of catalyst from entering the cooler 60, a sheet of screen material covers opening 61. The screen can be secured to opening 61 using a suitable method.

After catalyst is regenerated, there are gases entrained in the regenerated catalyst that increase amounts of byproducts in oxygenate to olefin conversion processes and make downstream product recovery more difficult. Entrained gases should be removed prior to the regenerated catalyst returning to reactor 10 to cut down on downstream product recovery resources. When the regenerated catalyst travels directly from regenerator 50 back to reactor 10, the range of flue gas entrained may preferably be between about 0.5 m$^3$/m$^3$ catalyst and about 0.8 m$^3$/m$^3$ catalyst.

The entrained gases from regenerator 50 may include O$_2$, CO, CO$_2$, N$_2$, NO$_x$, and H$_2$O. If the catalyst travels directly from regenerator 50 back to reactor 10, the entrained flue gases may comprise between about 8 and about 24 kg H$_2$O, between about 32 and about 40 kg O$_2$, between about 440 and about 530 kg N$_2$, between about 100 and about 150 kg CO$_2$ per 1000 m$^3$ of catalyst. The entrained flue gas may also comprise residual amounts of CO, NO$_x$, and sulfur compounds.

Preferably at least about 97 wt-% of the entrained gases are removed before returning to reactor 10. More preferably at least about 99 wt-% of the entrained gases are removed before returning to reactor 10.

After catalyst is regenerated, the catalyst enters a regenerated catalyst stripper 70. The regenerated catalyst stripper 70 may be contiguous with the lower section 56 of the regenerator 50 along with cooler 60 such that the regenerated catalyst stripper 70 is within the vessel of the catalyst regenerator 50. As seen in FIG. 2, in one embodiment, regenerated catalyst stripper 70 may be a cylindrical chamber connected to the lower section 56 of regenerator 50 such that regenerator 50 and regenerated catalyst stripper 70 form a single vessel with a common shell. Regenerator 50 and stripper 70 may also be two separate vessels connected by conduits directing the regenerated catalyst from the regenerator to the stripper. Regenerated catalyst is withdrawn from regenerator 50 and directed into stripper 70 where the catalyst may be fluidized by a gas and stripped by a stripping gas. The regenerated catalyst may be fluidized by fluidizing gas and may be impeded from direct downward flow by packing, or baffles. The assumed fraction of stripping gas entrained in the catalyst when it leaves the stripper 70 may be between about 0.3 and 0.7 and typically between about 0.4 and 0.6. In one embodiment, the stripping gas comprises nitrogen. The total stripping nitrogen used may preferably be between approximately 1 kg nitrogen/m$^3$ catalyst and about 4 kg nitrogen/m$^3$ of catalyst.

The regenerated catalyst may be fluidized in stripper 70 by an inert gas such as nitrogen for the stripping of the entrained gases from regeneration. The fluidizing gas may be introduced via distributor 80. The stripping gas may be introduced via distributor 90. In one embodiment the stripping gas comprises nitrogen. Alternatively, the catalyst may be dispersed in stripper 70 by packing. The stripping gas may be introduced via distributor 90 to the underside of the packing to strip the suspended regenerated catalyst. The assumed fraction of entrained stripping gas is between about 0.3 and 0.7.

In a preferred embodiment, the regenerated catalyst may be impeded from direct downward flow in the stripper 70 by baffles 75 as shown in FIG. 2. The baffles 75 comprise a perforated section 76 with openings that allow upward passage for the fluidizing gas to strip entrained gases from the regenerated catalyst. The baffles 75 may be sloped at an angle for drainage, especially during shutdown. Baffle 75 preferably does not extend across the entire cross-section of the stripping section 70. A downcomer area 77 is provided between an edge of each baffle 75 and an inside wall of stripper 70 for the catalyst to cascade from one baffle to the subjacent baffle in the stripper 70. An end plate 78 may be attached to the ends of each baffle 75 and extend downwardly from the edge of baffle to define a skirt which may serve to regulate the amount of any gas which may accumulate under each baffle. Arranging downcomer 77 area on opposite sides of stripper 70 on adjacent baffles 75 assures that the catalyst cascades downwardly through the stripping section from side to side. The spacing of perforations over the perforated section may be arranged in any manner that eliminates wide bands or areas that do not contain holes for delivery of the fluidization medium. It may be important that at least about 30% of the area of the perforated section 76 comprise openings to allow the passage of stripping medium therethrough and break up gas bubbles beneath the baffle. It is preferred that between about 50% and about 80% of the perforated section 76 comprise openings. It is further preferred that between about 65% and about 75% of perforated section 76 comprise openings. The baffles 75 are held in place by a support 79 which may be connected to the wall of stripping section 70 supporting the baffles from underneath. In one embodiment, support 79 may be wedge-shaped with one side of the wedge flush against the underside of each baffle 75.

Perforated section 76, with a high percentage of open area, allows the stripping medium to rise vertically upwardly through the stripper 70 through succeeding baffles 75 to engage the downwardly flowing catalyst wending through the stripping section in a transverse manner to promote better mixing between the stripping medium and the catalyst. In a preferred embodiment, the height of separation between succeeding baffles may be 61 cm (24 inches) apart but it may also be preferred to reduce the height to 46 cm (18 inches). In one embodiment, there may be an imperforate section 73 on the baffle 75. Imperforate section 73 may comprise a blank-off plate which rests on top of perforated section 76 of each baffle 75 below the downcomer 77 of the superjacent baffle 75. Preferably, blank-off plate comprising part or all of imperforate section 73 may be secured to perforated section 76. The imperforate section further promotes the horizontal movement of the catalyst by forcing it to change direction after coming through a superjacent downcomer area 77. The imperforate section 73 comprises between about 10% and about 30% of the cross-sectional area of the stripper with about 20% being preferred. Perforated section 76 of the baffle 75 not covered by the imperforate section 73 in an embodiment comprises about 40% to about 80% of the cross-sectional area of the stripper 70 with about 60% being preferred. The downcomer section 77 comprises between about 10% and about 30% of the cross-sectional area of the stripper 70 with about 20% being preferred.

Stripping gas and fluidizing gas may be introduced into stripper 70 via different distributors or stripping gas introduced via only one distributor may also act as fluidizing gas. Stripping gas may be introduced via distributor 80 and fluidizing gas may be introduced via distributor 90. In a preferred embodiment, stripping gas and fluidizing gas for stripper 70 comprise nitrogen gas. Both stripping gas distributor 80 and fluidizing gas distributor 90 introduce nitrogen to the underside of baffles 75 by jets. In an embodiment, slightly, downwardly sloped jets 82 on stripping gas distributor 80 direct nitrogen toward a centerline of the stripper 70 to produce upward gas flow under the perforated sections 76 of the baffles 75. Jets 91 on fluidizing gas distributor 90 direct nitrogen upwardly toward baffles 75 to fluidize regenerated catalyst. Jets 92 on the fluidizing gas distributor 90 direct nitrogen downwardly toward a regenerated catalyst standpipe 100 to keep catalyst fluidized in standpipe 100. Having two distributors of nitrogen keeps the flow density constant throughout stripper 70 to optimize stripping. The flow rate of stripping gas from stripping gas distributor 80 may be between about three times and about five times greater than the flow rate of fluidizing gas from fluidizing gas distributor 90. The stripping gas flow rate may more preferably be about four times greater than fluidizing gas flow rate.

Stripping gas and fluidizing gas introduced into stripper 70 for the stripping of the regenerated catalyst travel upwardly through the stripper 70 and regenerator 50 and exit along with regenerator flue gases through conduit 58. After the regenerated catalyst travels downwardly through stripper 70 by means of transverse movement along the baffles 75, the catalyst may be funneled into the regenerated catalyst standpipe 100 through funnel 95 at the bottom of the stripping section 70. The regenerated catalyst that has been stripped of gases entrained during regeneration may be returned back to reactor 10 by the regenerated catalyst standpipe 100.

A system for regenerating spent catalyst used in converting oxygenate-containing feedstock to olefins comprises a catalyst regenerator, a regenerated catalyst stripper having a regenerated catalyst inlet, a stripping gas distributor, and a stripped regenerated catalyst outlet. In one embodiment of the invention, a regenerated catalyst stripper contains a plurality of baffles. Each one of the baffles may have a perforated section. Each baffle may be mounted and spaced apart overlappingly on alternate sides of the regenerated catalyst stripper. The stripping gas in the stripper may comprise nitrogen. There may be a common outlet for gases from said regenerated catalyst stripping section and the regenerator, where the regenerated catalyst stripping section is in fluid communication with the regenerator. The stripping distributor may be below said regenerated catalyst inlet. The catalyst inlet may be near the top of the stripper. The catalyst outlet may be near the bottom of the stripper.

EXAMPLE

An experimental simulation was conducted for an MTO unit to more fully demonstrate the stripping of entrained gases from regenerated catalyst before returning the catalyst to the reactor. The catalyst comprises a silicoaluminophosphate (SAPO) molecular sieve. SAPO molecular sieves comprise a molecular framework of $SiO_2$, $Al_2O_3$, and $P_2O_5$ tetrahedral units. The catalyst may be circulated at a rate of about 136,077 kg/hr (300,000 lb/hr). The coke on the spent catalyst is about 3.0 wt-% and the coke on the regenerated catalyst is about 0.3 wt-%. The amount of coke oxidized in the regenerator is 3,659 kg/hr (8,066 lb/hr).

MTO unit is designed to convert methanol to light olefins. In this particular example, we have assumed the following composition: 5.0 wt-% water, 95 wt-% methanol, 0.2 wt-% ethanol, 1000 wppm higher alcohols and 30 wppm dimethyl ether.

The entrained components on the regenerated catalyst returned to reactor 10 without passing through regenerated catalyst stripper 70 per 1000 $m^3$ catalyst are as follows: 16 kg $H_2O$, 37 kg $O_2$, 462 kg $N_2$ and 124 kg $CO_2$. After regenerated catalyst passes through the stripper 70, the entrained components per 1000 $m^3$ catalyst are as follows: 0.16 kg $H_2O$, 0.37 kg $O_2$, 4.6 kg $N_2$, 1.2 kg $CO_2$.

The above example is only intended to illustrate certain aspects of the present invention and is not meant to be limiting.

What is claimed is:

1. A method of processing spent catalyst from an oxygenate to olefins conversion process comprising:
    regenerating said spent catalyst from an oxygenate to olefin conversion process to provide regenerated catalyst; and
    stripping said regenerated catalyst of gases entrained during said regenerating step.
2. The method according to claim 1, wherein said stripping step is accomplished with nitrogen gas.
3. The method according to claim 1, further comprising stripping said spent catalyst of hydrocarbons before said regenerating step.

4. The method according to claim 1, wherein said entrained gases comprise oxygen, carbon dioxide, and carbon monoxide.

5. A method of converting oxygenate to olefins comprising:

charging a reactor with catalyst;

feeding said oxygenate into said reactor;

contacting said oxygenate with said catalyst in said reactor and converting said oxygenate to said olefins while spending said catalyst;

regenerating said spent catalyst by burning combustion gases; and stripping said regenerated catalyst of gases entrained in said regenerating step.

6. The method according to claim 5, wherein said stripping step is accomplished with nitrogen gas.

7. The method according to claim 6, further comprising said stripping gases combining with said combustion gases and discharging from a common outlet.

* * * * *